United States Patent [19]

Corbet

[11] Patent Number: 4,755,614

[45] Date of Patent: Jul. 5, 1988

[54] PREPARATION OF HERBICIDES CONTAINING A PHOSPHONATE GROUP FROM INTERMEDIATE BENZOXAZINES

[75] Inventor: Jean-Pierre Corbet, Ecully, France

[73] Assignee: Rhone-Poulenc Agrochimie, Lyons, France

[21] Appl. No.: 841,588

[22] Filed: Mar. 20, 1986

[30] Foreign Application Priority Data

Mar. 21, 1985 [FR] France ............................... 85 04433

[51] Int. Cl.[4] ............................ C07F 9/38; C07F 9/40
[52] U.S. Cl. .................................... 558/134; 544/90; 558/87; 558/168; 558/169; 558/170; 558/174; 558/386; 560/39; 562/444; 564/15
[58] Field of Search .............. 558/134, 168, 169, 170, 558/174, 386; 560/39; 562/444; 564/15

[56] References Cited

U.S. PATENT DOCUMENTS 3,082,112  3/1963  Hemwall ........................... 106/287

FOREIGN PATENT DOCUMENTS 2144425A  3/1985  United Kingdom .

OTHER PUBLICATIONS

Dihydro-1,3-Oxazines as Antitumor Agents, M. E. Kuehne and E. A. Konopka (3-1962).

Primary Examiner—Richard L. Raymond
Attorney, Agent, or Firm—Morgan & Finnegan

[57] ABSTRACT

Preparation of intermediates for herbicides of formula

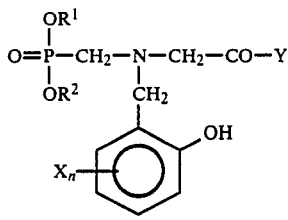

(I)

by the reaction of organic phosphites with benzoxazines of formula

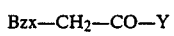

(II)

in which
Bzx denotes the radical of formula:

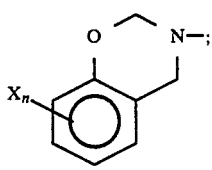

X is a usual substituent of phenols
n is an integer from 0 to 4
$R^1$ and $R^2$ are H or such that $OR^1$ and $OR^2$ are hydrolyzable
Y is —OM or —$NR^3R^4$
M is H or is such that COOM is a salt or an ester
$R^3$ and $R^4$ are H or a hydrocarbon radical, and one of them can be $R^5$—$SO_2$—, and
$R^5$ is a hydrocarbon radical, substiuted if appropriate. Products obtained by the process and their use as herbicides.

10 Claims, No Drawings

PREPARATION OF HERBICIDES CONTAINING A PHOSPHONATE GROUP FROM INTERMEDIATE BENZOXAZINES

The present invention relates to a new process for the preparation of intermediate products for the manufacture of herbicides, and to some of these intermediates as new products.

According to the process according to the invention, a product of formula

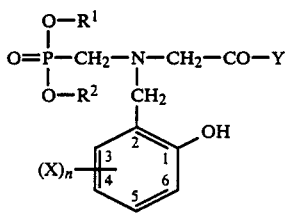

is prepared by the reaction of phosphites of formula

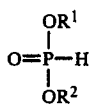

with a benzoxazine of formula Bzx-CH$_2$-CO-Y (II) in which formulae

Bzx denotes the radical of formula

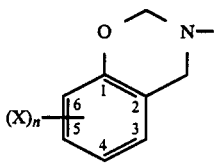

X denotes a substituent of phenols which is known per se, such as, for example, a halogen (especially fluorine, chlorine, bromine or iodine) atom or a hydrocarbon radical (especially alkyl, alkenyl, alkynyl, cycloalkyl or aryl) optionally substituted and preferably containing from 1 to 4 carbon atoms, it being understood that the various substituents X, when several are present, can be identical or different and that, preferably, at least one substituent is situated in position 4, a second substituent, when one is present, being situated preferably in position 6, n is an integer, positive or zero, less than or equal to 4, preferably equal to 1 or 2, R$^1$ and R$^2$, identical or different, denote the hydrogen atom or are such that OR$^1$ and OR$^2$ are hydrolyzable groups, and R$^1$ and R$^2$ can be, in particular, an alkyl or aryl radical (preferably alkyl or phenyl), optionally substituted, especially by substituents such as those indicated for R$_5$ hereinafter; generally, they contain from 1 to 12 carbon atoms and preferably from 1 to 8 carbon atoms, Y is an —OM or —NR$^3$R$^4$ residue, M is the hydrogen atom or an alkali metal atom or ammonium or an atom or group such that —COOM constitutes a salt or ester function (preferablyy an ester of an alkanol containing from 1 to 4 carbon atoms), R$^3$ and R$^4$, which are identical or different, denote the hydrogen atom or a hydrocarbon radical (especially alkyl, alkenyl, alkynyl, cycloalkyl, especially cyclohexyl or aryl or aralkyl), one of them being capable of being a sulphonyl group R$^5$—SO$_2$—(R$^3$ and R$^4$ generally contain from 1 to 18 carbon atoms, preferably from 1 to 4 carbon atoms), R$^5$ denotes a hydrocarbon radical, especially alkyl, aryl or cycloalkyl, these various radicals being capable of being substituted, if appropriate; as substituents, there can be mentioned, in particular, halogen atoms and phenyl, cyano, alkyl, alkoxy or alkyl carboxylate groups, in which the alkyl groups preferably contain from 1 to 4 carbon atoms; in most cases R$^5$ contains from 1 to 18 carbon atoms, preferably from 1 to 7 carbon atoms, and more especially from 3 to 7 carbon atoms when a cycloalkyl group is involved; preferably, the group in question is an alkyl radical containing from 1 to 4 carbon atoms, optionally halogenated, especially chlorinated or fluorinated, for example CF$_3$.

The products of formula (I) are new products which form part of the invention. In general, the products of formula (II) form part of the invention except when any one of the following conditions a, b or c, taken in isolation, is fulfilled:

(a) R$^3$ and R$^4$ are the hydrogen atom and n is 1 and X is Br of CH$_3$ or methoxy in position 4, (b) M is methyl, n is 1 and X is methoxy in position 4, (c) M is the hydrogen atom, n is 1, and X is a tertbutyl group in position 4.

The reaction of a phosphite with a product of formula (II) is carried out either in the presence or in the absence of a solvent, at a temperature of between 40° and 180° C., preferably between 70° and 130° C.

Hydrocarbons which are halogenated or otherwise, ethere and esters (especially alkyl alkanoates, and more especially ethyl acetate), and nitriles, can be mentioned, without implying any limitation, as solvents which can be used.

The proportion of the reactants is generally such that the molar ratio phosphite/compound of formula (II) is between 0.9 and 2, preferably between 1 and 1.5.

The processes for the preparation of compounds of forumla (II) also form part of the invention.

According to one of these processes, the products of formula (II), in which X, n and Y have the meaning given for the formula (I), but Y is preferably the radical -OM, are conveniently prepared by the reaction of a phenol of forumla

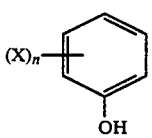

(in which X and n have the meanings which have been given already and in which at least one carbon of the phenyl ring ortho to the * with formaldeyhde and an amino acid derivative of formula

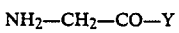

NH$_2$—CH$_2$—CO—Y   (IV)

*hydroxyl group is unsubstituted
(in which Y has the meaning given above), the molar quantity of formaldehyde being greater than or equal to twice the number of moles of the compound of formula (III) or (IV) which is in a molar quantity which is less than or equal to the other. The reaction temperature is generally between 0° and 120° C., preferably between 10° and 80° C. It is advantageous to carry out the reaction in the presence of a basic agent; the basic agent used may be an organic or preferably inorganic base, for example an alkali metal or alkaline-earth metal hydroxide or carbonate, and more specifically a sodium or potassium derivative. The quantity employed is generally between 0.01 and 5 mol %, preferably between 0.05 and 1%, the percentages being based on the engaged phenol of formula (III); in the case where Y is an OH group, this quantity needs to be increased by the quantity of basic agent required to neutralize the acid group. The reaction medium is advantageously alcoholic but can also contain other organic solvents or even water, preferably a solvent for the reactions of formula (III) and/or (IV). Formaldehyde can be used in the form of a precursor, such as paraformaldehyde.

According to another process for the preparation of compounds of formula (II), expecially of compounds in whose formula Y is —NR³R⁴, and more especially those in which Y is —NR³ (—SO₂—R⁵), the said compounds are prepared from analogous compounds of the formula (II) in which Y is OM.

Thus, the invention relates to a process for the preparation of a compound of formula:

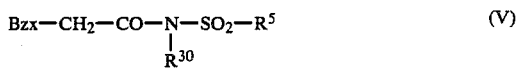

in which formula Bzx, R⁵ and n are such as defined for the formulae (I) and (II), and R³⁰ as the same meaning as R³, with the exception of a hydrogen atom, this process consisting in reacting a a sulphonamide of formula:

with a mixed anhydride of formula:

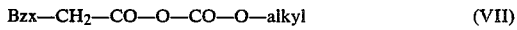

itself obtained by the reaction of a product of formula:

(preferably in salt form) with an alkyl chloroformate (CL—CO—O—alkyl; where the alkyl preferably contains 1 to 4 carbon atoms). The product of formula (VIII) is advantageously used in the form of an alkali metal or ammonium salt. The reaction is advantageously carried out at a temperature between −30° and +30° C. in the presence of a solvent and, preferably, in the presence of phase transfer catalysts such as quaternary ammoniumsalts of strong acids (halides, sulphates or phosphates); when a solvent is used in which the salts formed during the reaction are insoluble, then it is sufficient to isolate the reaction product by filtration. Thus, ethers and esters, especially tetrahydofuran and ethyl acetate, can be used as solvents.

The reaction of the mixed anhydride of formula (VII) with the sulphonamide R₅—SO₂—NH—R³⁰ is advantageously carried out in a two-phase medium consisting of water and an organic solvent, in the presence of an alkaline agent and a phase-transfer catalyst. The temperature is generally between 0° and 50° C. Quaternary ammonium salts of a strong acid, such as tetraalkylammonium or trialkylaralkylammonium halides or sulphates, can be mentioned as a possible phase-transfer catalyst (which is generally used in a proportion of 0.1 to 10% by weight relative to the mixed anhydride). The alkaline agent used is advantageously an alkali metal or alkaline earth metal or ammonium hydroxide or carbomate, preferably an alkali metal hydroxide. The organic solvent used is a water-immiscible organic solvent, for example $CH_2CL_2$ or esters (especially ethyl acetate).

The preparation of herbicidal compounds from compounds of formula (I) is usually carried out by hydrogenolysis of the ortho-hydroxybenzyl group of formula:

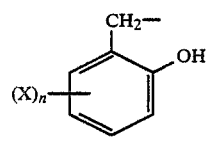

and this leads to the formation of compounds of formula:

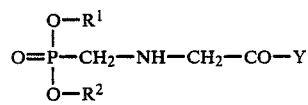

which can either be usd as such, or can be converted to various derivatives by means of reactions such as hydrolysis and/or salt formation and/or esterification, and others. The herbicidal compounds which can be obtained in this manner are, generally, known compounds.

This reaction of hydrogenolysis of the compounds of formula (I) is advantageously carried out in an aqueous or alcoholic medium at ambient or higher temperature, at atmospheric or higher pressure. The usual catalysts for hydrogenolysis of the radical benzyl or substituted benzyl can be used as a catalyst. Palladium, platinum and Raney nickel may be mentioned as suitable catalysts. This catalyst may be used with or without an inert support. The abovementioned metals, especially palladium and platinum, can also be used in the form of salts, hydroxides or oxides, which are converted to the corresponding metal by the action of hydrogen. Palladium-based catalysts such as palladium on charcoal or palladium on barium sulphate, or palladium hydroxide on charcoal can be used as a preferred hydrogenolysis catalyst. When the reaction is finished, the catalyst can be separated off by filtration and the filtrate can be evaporated down; this produces a herbicidal product of good purity (this hydrogenolysis is known per se in the case of a nitrogen atom substituted by a benzyl group).

When it is intended to prepare unesterified forms of known herbicides such as, for example, N-phosphonomethylglycine itself, the product of formula (I) (when R¹ and R² are other than the hydrogen atom) may be hydrolyzed completely or partially in a known manner, for example by heating with an aqueous solution of an acidic or alkaline agent, especially alkali metal or alkaline earth metal hydroxide or carbonate, hydrochloric, hydrobromic, sulphyric, phosphoric, perchloric or arylsulphonic acids. This hydrolysis can also be accompanied by a salt formation or by a conversion of other herbicidal derivatives.

The following examples, which are given without implying any limitation, illustrate the invention and show how it can be implemented practically.

In these examples, B°z°x° denotes the radical of formula Bzx in which n is equal to zero.

EXAMPLE 1

Paraformaldehyde (2.62 g; 87.28 millimoles), methanol (3.5 cc) and solid potassium hydroxide (0.05 g) are placed in a 50-cc round flask fitted with a magnetic stirrer, a thermometer, a dropping funnel and a condenser, and maintained under argon. The materials are dissolved by being heated and are then cooled. A solution of ethyl glycinate (4.50 g; 43.64 millimoles) in methanol (1 cc) is then run in over 5 minutes into the reaction medium at 20° C. Para-cresol (4.71 g; 43.64 millimoles) is then added and the mixture is heated under reflux for approximately 20 minutes, after which time the methanol is removed under a reduced pressure of 0.2 bar and a temperature in the region of 50° C.

The residue is chromatographed on a silica column (eluant: hexane-ethyl acetate).

After removal of the solvents under reduced pressure (0.2 bar) and drying, an oily product (3.65 g; 15.5 millimoles) of formula 5-methyl-B°z°x°—CH$_2$—COOC$_2$H$_5$ is obtained, the structure of which is confirmed by spectroscopy (infrared absorption based at 1750 cm$^{-1}$).

This oily product (3.5 g; 14.8 millimoles) and diethyl phosphite (2.07 g; 14.8 millimoles) are introduced into a 10-cc round flask. The mixture is heated for 55 minutes to a temperature in the region of 80° C. Diethyl phosphite (0.20 g; 1.48 millimole) is then added and the mixture is heated to about 80° C. for 35 minutes. Excess diethyl phosphite is removed under reduced pressure (0.27 bar) at a temperature in the region of 40° C.

The residue consists of a phosphonate of formula:

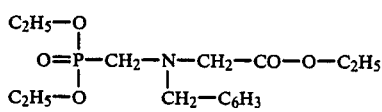

(4-methyl-1-hydroxy)
(The position of the substituents being numbered as in formula (I))

This phosphonate (1.0 g; 2.54 millimoles) is dissolved in 1.01 N methanolic sodium hdyroxide (5.05 cc; 5.05 millimoles). The mixture is heated for 3 hours at a temperature in the region of 80° C. The methanol is removed under reduced pressure (0.2 bar) at a temperature in the region of 40° C. The residue is dissolved in distilled water (3 cc) and then the aqueous phase obtained is washed with methylene chloride. The aqueous phase is then acidified to pH=2 with 6 N HCL and then extracted with methylene chloride (3×30 cc). The combined organic extracts are dried over magnesium sulphate. After separation by filtration and removal of methylene chloride under reduced pressure (0.2 bar), 550 mg (1.59 millimole) are obtained in the form of a white solid melting at 102° C., with a purity of about 90%, and having the formula

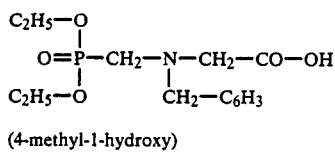

(4-methyl-1-hydroxy)

This product can be hydrogenolyzed to a product of formula:

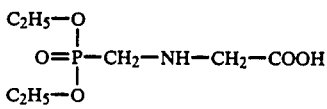

using known methods.

EXAMPLE 2

Paraformaldehyde (6.0 g: 0.2 mole), methanol (8 cc) and solid potassium hydroxide (0.1 g) are placed in a 50-cc round flask. The materials are dissolved by being heated and are then cooled.

A solution of sodium glycinate [prepared from glycine (7.50 g; 0.1 mole)], powdered sodium hydroxide (4.0 g; 0.1 mole) and methanol (30 cc)) is then added dropwise to the above solution at 20° C., with stirring. The mixture is stirred for 20 minutes at 20° C. Phenol (9.4 g; 0.1 mole) is then added and the mixture is heated to 60° C. After 45 minutes, the mixture is cooled to 20° C. and the precipitate is filtered off and then washed with ethyl ether (3×10 cc) and is dried.

A white powder (8.47 g) is obtained and is purified at 60° C. by being stirred with methanol (25 cc) for one hour. It is then virtually completely dissolved. The temperature is then allowed to return to 20° C. The precipitate formed is filtered off, washed with ethyl ether (3×20 cc) and is dried under reduced pressure (0.27 bar; 20° C.).

In this manner, a benzoxazine, of formula B°z°x°—CH$_2$—COONa (4.55 g; 21.1 millimoles) is obtained in a purity of 90%.

This benzoxazine can be treated with a phosphite as indicated in Example 1 to obtain a product of formula (I).

EXAMPLE 3

Paraformaldehyde (6.0 g; 0.2 mole), methanol (8 cc) and a potassium hydroxide pellet are put in a 100-cc round flask. The medium is heated for 15 minutes at 45° C. and then cooled to 15° C. A solution of sodium glycinate (prepared from glycine (7.50 g; 0.1 mole), powdered sodium hydroxide (4.00 g; 0.1 mole) and methanol (30 cc)) is then added over 20 minutes to the above solution at 20° C., with stirring. The mixture obtained is stirred for 30 minutes at 20° C.

Para-cresol (10.81 g; 0.1 mole) is then added and the mixture is heated for 35 minutes at 50°-60° C. and is cooled to 20° C. The precipitate is filtered off and is then washed with ether 3×25 cc) and is dried.

This produces practically pure benzoxazine (13.26 g; 57.8 millimoles) (yield: 57.8%) which has the formula 4-methyl-B°z°x°—CH$_2$—COONa(infrared absorption band at 1600 cm$^{-1}$ and 1400 cm$^{-1}$).

EXAMPLE 4

Paraformaldehyde (18.0 g; 0.6 mole), methanol (24 cc) and solid potassium hydroxide (0.3 g) are put in a 500-cc round flask and are heated for 15 minutes at 45°-50° C. The mixture is cooled to 15° C. and triethylamine (4.2 cc; 3.03 g; 30 millimoles) is added.

A solution of sodium glycinate [prepared from glycine (22.52 g; 0.3 mole)], methanol (90 cc) and solid sodium hydroxide (12.0 g; 0.3 mole)) is added dropwise to the above solution at 15° C. The medium is then stirred for 1 hour at 20° C. 2,4-Dichlorophenol (48.9 g; 0.3 mole) is then added and the mixture is heated under reflux for 3 hours and is then cooled to 20° C.

After filtration and a treatment similar to that described in Example 3, a benzoxazine of formula 4,6-dichloro-B°z°x°—$CH_2$—COONa (42.0 g; 0.148 mole) is obtained (49.3% yield) and its structure is confirmed by spectroscopy.

EXAMPLE 5

By using a method similar to that described in Example 4, but starting from
- a solution of paraformaldehyde (18.0 g; 0.6 mole) and potassium hydroxide 0.3 g) in methanol, on the one hand,
- a solution of sodium glycinate prepared from glycine (22.52 g; 0.3 mole), sodium hydroxide (12.0 g; 0.3 mole) in methanol (90 cc), on the other hand, and
- para-chlorophenol (38.57 g; 0.300 mole),
- a pure bezoxazine of the formula 4-chloro-B°z°x°—$CH_2$—COONa (24.5 g; 98.3 millimoles) is obtained 32.7% yield). The benzoxazines of Example 3 to 5 can be treated with phosphites as indicated in Examples 1 and 2.

EXAMPLE 6

The benzoxazine prepared in Example 3 (1.15 g; 5 millimoles),
dry ethyl acetate (5 cc), and
tetra(n-butyl)ammonium chloride (0.11 g) are placed in a 20-cc round flask.

The suspension obtained is cooled at 10° C. Ethyl chloroformate (0.48 cc; 5 millimoles) is added at −10° C. and then the temperature is allowed to rise to 20° C. The mixture is stirred for 2 hours and is then cooled to 10° C.

The product of formula 4-methyl-B°z°x°—$CH_2$—CO—O—CO—O—$C_2H_5$ is formed.

N-Methyl(methanesulphonamide) (0.59 g; 5.5 millimoles) is then added and 50% (weight/weight) aqueous sodium hydroxide (0.44 g; 5.5 millimoles) is then run in dropwise while the temperature is maintained at +10° C. After 25 minutes, the mixture is diluted with water (5 cc). The organic phase is collected and the aqueous phase is extracted with ethyl acetate (4×10 cc). The combined organic extracts are washed with distilled water (10 cc) and are dried over sodium sulphate. After separation by filtration and concentration under reduced pressure (0.2 bar) at 30° C., an oily residue (1.25 g) is obtained, which crystallizes slowly at about 4° C. It is purified by recrystallization from a mixture of ethyl acetate and cyclohexane and yields a product melting at 134° C. and having the formula 4-methyl-B°z°x°—$CH_2$—CO—N($CH_3$)—$SO_2$—$CH_3$ The benzoxazine thus prepared (0.317 g; 1.062 millimoles), diethyl phosphite (0.147 g; 1.065 millimole) and toluene (1 cc) are introduced into a 10-cc round flask.

The mixture is heated at 80° C. for 2 hours and then under reflux for 5 hours, and then toluene is removed under reduced pressure (0.2 bar) at 30° C.

The residue (0.450 g) is chromatographed on silica (10 g), a methylene chloride/methanol mixture being used as eluant. After removal of the solvents under reduced pressure (0.2 bar) at 30° C. and drying under a high vacuum (27 millibars; 20° C.), a white solid which melts at 79° C. is obtained (41.6% yield), which has the formula:

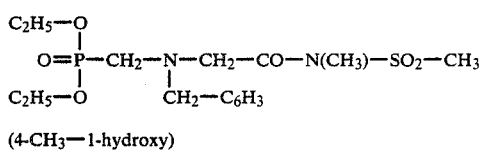

(4-$CH_3$—1-hydroxy)

This product can be hydrogenolyzed as indicated in Example 1.

I claim:

1. A process for preparing a product of the formula:

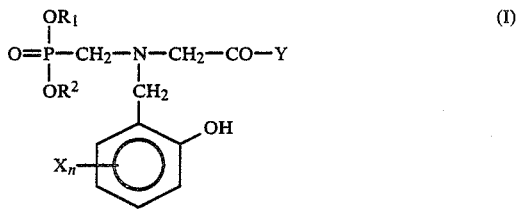 (I)

by reacting a phosphite of the formula:

with a benzoxazine of the formula:

Bzx—$CH_2$—CO—Y wherein:
Bzx is

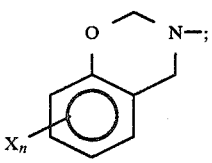

X is halogen selected from the group consisting of fluorine, chlorine, bromine and iodine, or substituted or unsubstituted alkyl, alkenyl, alkynyl, chcloalkyl or aryl; n is an integer from 0 to 4;
each of $R^1$ or $R^2$ is hydrogen, or such that $OR^1$ or $OR^2$ is hydrolyzable group of 1 to 12 carbons atoms; and
Y is —OM or—$NR^3R^4$, where M is an alkali metal or ammonium or—COOM constitutes an ester; and each of $R^3$ or $R^4$, which may be identical or different, is hydrogen, a hydrocarbon radical selected from the group consisting of alkyl, alkenyl, alkynyl, cycloalkyl, aryl and aralkyl of 1 to 18 carbon atoms or one of $R^3$ or $R^4$ is $R^5$—$SO_2$—where $R^5$ is alkyl, aryl, or cycloalkyl optionally substituted with halogen, phenyl, cyano, alkoxy, or alkyl carboxylate.

2. A process according to claim 1 wherein X is a hydrocarbon radical of 1 to 4 carbon atoms selected from the group consisting of alkyl, alkenyl, alkynyl and cycloalkyl and n is 1.

3. A process according to claim 1 wherein X is a hydrocarbon radical of 1 to 4 carbon atoms selected from the group consisting of alkyl, alkenyl, alkynyl and cycloalkyl; and n is 2 and substituted at position 4 and 6 on the benzene ring.

4. A process according to claim 1 wherein each of $R^1$ or $R^2$ is alkyl or phenyl of 1 to 8 carbon atoms.

5. A process according to claim 1, wherein each of $R^3$ or $R^4$ is alkyl having 1 to 4 carbon atoms.

6. A process according to claim 1 wherein $R^5$ contains 1 to 7 carbon atoms.

7. A process according to claim 1, wherein $R^5$ is —$CF_3$.

8. A process according to claim 1, wherein the temperature of the reaction is between about 40° C. to 180° C.

9. A process according to claim 1 wherein the temperature of the reaction is between about 70° C. to 130° C.

10. A process according to claim 1, wherein the reaction is carried out in the presence of a solvent selected from the group consisting of hydrocarbons, halogenated hydrocarbons, ethers, esters, and nitriles.

* * * * *